(12) United States Patent
Nishimori et al.

(10) Patent No.: US 10,071,959 B2
(45) Date of Patent: Sep. 11, 2018

(54) POLYTHIOL COMPOUND AND METHOD FOR PRODUCING SAME

(71) Applicant: MITSUBISHI GAS CHEMICAL COMPANY, INC., Tokyo (JP)

(72) Inventors: Yoshihiko Nishimori, Tokyo (JP); Teruo Kamura, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/917,120

(22) PCT Filed: Oct. 28, 2014

(86) PCT No.: PCT/JP2014/078548
§ 371 (c)(1),
(2) Date: Mar. 7, 2016

(87) PCT Pub. No.: WO2015/064548
PCT Pub. Date: May 7, 2015

(65) Prior Publication Data
US 2016/0229798 A1   Aug. 11, 2016

(30) Foreign Application Priority Data

Nov. 1, 2013   (JP) .................................. 2013-228486

(51) Int. Cl.
| | | |
|---|---|---|
| *C07C 321/14* | (2006.01) | |
| *C08G 18/38* | (2006.01) | |
| *C08G 18/80* | (2006.01) | |
| *C08G 75/06* | (2006.01) | |
| *C07C 335/08* | (2006.01) | |
| *G02B 1/04* | (2006.01) | |
| *C08G 18/76* | (2006.01) | |
| *C08G 18/24* | (2006.01) | |
| *C07C 319/22* | (2006.01) | |
| *C08L 81/04* | (2006.01) | |
| *C08L 75/04* | (2006.01) | |

(52) U.S. Cl.
CPC .......... *C07C 321/14* (2013.01); *C07C 319/22* (2013.01); *C07C 335/08* (2013.01); *C08G 18/246* (2013.01); *C08G 18/3868* (2013.01); *C08G 18/3874* (2013.01); *C08G 18/3876* (2013.01); *C08G 18/7642* (2013.01); *C08G 18/8054* (2013.01); *C08G 75/06* (2013.01); *G02B 1/04* (2013.01); *G02B 1/041* (2013.01)

(58) Field of Classification Search
CPC ... C07C 321/14; C07C 335/08; C07C 319/22; G02B 1/04; G02B 1/041; C08L 81/04; C08L 75/04; C08G 75/06; C08G 18/3868; C08G 18/3876; C08G 18/246; C08G 18/7642; C08G 18/3874; C08G 18/8054

See application file for complete search history.

(56) References Cited

U.S. PATENT DOCUMENTS

| | | | |
|---|---|---|---|
| 5,087,758 A | 2/1992 | Kanemura et al. | |
| 6,117,923 A | 9/2000 | Amagai et al. | |
| 2009/0264613 A1 | 10/2009 | Kuma et al. | |
| 2011/0176220 A1 | 7/2011 | Kuma et al. | |
| 2012/0309932 A1 | 12/2012 | Takemura et al. | |
| 2015/0203633 A1 | 7/2015 | Takemura et al. | |

FOREIGN PATENT DOCUMENTS

| | | |
|---|---|---|
| CN | 1405198 | 3/2003 |
| CN | 102633980 | 8/2012 |
| CN | 102762637 | 10/2012 |
| EP | 2845847 A1 | 11/2015 |
| EP | 2845848 A1 | 11/2015 |
| EP | 3 012 277 | 4/2016 |
| JP | 1-268673 | 10/1989 |
| JP | 2-270859 | 11/1990 |
| JP | 10-298287 | 11/1998 |
| JP | 11-80308 | 3/1999 |
| JP | 2002-226456 | 8/2002 |
| JP | 2005-170820 | 6/2005 |
| JP | 2012-167198 | 9/2012 |
| JP | 2013-10772 | 1/2013 |
| WO | 2007/129449 | 11/2007 |
| WO | 2011/105320 | 9/2011 |

OTHER PUBLICATIONS

Jaffrennou et al.; Characterization, structural transitions and properties of a tighly crosslinked polythiourethane network for optical applications; ePolymers 2005, No. 082; http://www.e-polymers.org; ISSN 1618-7229; pp. 1-19.*
International Search Report issued in PCT/JP2014/078548, dated Dec. 22, 2014.
Shashoua et al., "The Homopolymerization of Monoisocyanates", JACS, 1959, vol. 82, pp. 866-873.

* cited by examiner

*Primary Examiner* — Rabon A Sergent
(74) *Attorney, Agent, or Firm* — Greenblum & Bernstein, PLC

(57) ABSTRACT

According to the present invention, a polythiol compound having a total nitrogen content of 50 to 600 ppm inclusive can be provided. According to the present invention, a method for producing the polythiol compound can also be provided, said method being characterized by comprising the steps of: reacting a polyalcohol with thiourea to prepare a thiuronium salt; and adding at least one base selected from the group consisting of hydrazine (hydrate), ammonia and an amine and an inorganic base (that is different from hydrazine (hydrate) or ammonia) to the thiuronium salt in the presence of an organic solvent to hydrolyze the thiuronium salt.

9 Claims, No Drawings

POLYTHIOL COMPOUND AND METHOD FOR PRODUCING SAME

TECHNICAL FIELD

The present invention relates to a polythiol compound containing a small amount of a nitrogen component and a method for producing the compound, and particularly relates to a polythiol compound suitably used for optical materials such as a plastic lens, a prism, an optical fiber, an information recording substrate and a filter, in particular for a plastic lens, and a method for producing the compound.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, many organic compounds having a sulfur atom have been reported as raw materials of plastic lenses for eyeglasses. In particular, polythiol compounds having a sulfur atom are known to be useful compounds, and for example, such polythiol compounds are reacted with isocyanate to be used as polythiourethane resin having excellent impact resistance, or are reacted with episulfide to be used as resin having an excellent refractive index (Patent Documents 1 and 2). However, polythiol compounds are easily colored by long-term preservation or exposure to high temperature during transportation or the like, and it causes the problem of color phase deterioration of optical materials obtained by polymerizing the polythiol compounds.

PRIOR ART DOCUMENTS

Patent Documents

Patent Document 1: Japanese Laid-Open Patent Publication No. H02-270859
Patent Document 2: Japanese Laid-Open Patent Publication No. H10-298287

SUMMARY OF THE INVENTION

Problems to be Solved by the Invention

The problem to be solved by the present invention is to provide a polythiol compound for optical lenses, wherein color phase deterioration due to long-term preservation or high temperature is not easily caused, and a method for producing the compound.

Means for Solving the Problems

The present inventor diligently made researches in order to solve the above-described problem, and found that color phase deterioration of polythiol compounds is caused by a nitrogen component contained therein. The present inventor further made researches, and found that a polythiol compound containing a small amount of a nitrogen component, wherein color phase deterioration is not easily caused for a long period of time, can be obtained by combined use of an amine and an inorganic base in the hydrolysis step in the production of a thiuronium salt and then a polythiol therefrom, and thus the present invention was achieved.

Specifically, the present invention is as follows:

<1> A polythiol compound having a total nitrogen content of 50 to 600 ppm.

<2> The polythiol compound according to item <1>, which has a structure represented by formula (1) below:

$$HS\diagup\diagdown_S\diagup\diagdown_S\diagup\diagdown^{SH}_{SH} \quad (1)$$

<3> A composition for optical materials comprising the polythiol compound according to item <1> or <2> and a polyisocyanate compound.

<4> A composition for optical materials comprising the polythiol compound according to item <1> or <2> and an episulfide compound.

<5> An optical material obtained by polymerizing and curing the composition for optical materials according to item <3> or <4>.

<6> A method for producing the polythiol compound according to item <1> or <2>, which comprises reacting a polyalcohol with thiourea to prepare a thiuronium salt; and adding at least one base selected from the group consisting of hydrazine (hydrate), ammonia and an amine and an inorganic base (with proviso that hydrazine (hydrate) and ammonia are excluded) to the thiuronium salt in the presence of an organic solvent to hydrolyze the thiuronium salt.

<7> The method for producing the polythiol compound according to item <6>, wherein the organic solvent is at least one selected from the group consisting of diethyl ether, benzene, toluene, xylene, dichloroethane, chloroform and chlorobenzene.

<8> The method for producing the polythiol compound according to item <6> or <7>, wherein the inorganic base is at least one selected from the group consisting of sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide.

<9> The method for producing the polythiol compound according to any one of item <6> to <8>, wherein the amount of the at least one base selected from the group consisting of hydrazine (hydrate), ammonia and amine to be added is 0.4 to 1.2 equivalents relative to the thiuronium group in the thiuronium salt.

Advantageous Effect of the Invention

According to the present invention, it is possible to obtain a polythiol compound for optical materials, wherein color phase deterioration due to long-term preservation or high temperature is not easily caused.

EMBODIMENTS FOR CARRYING OUT THE INVENTION

The present invention is a polythiol compound having a total nitrogen content of 50 to 600 ppm, and in consideration of preparation of thick lenses such as powerful lenses, the total nitrogen content is more preferably 50 to 300 ppm, and particularly preferably 50 to 150 ppm. There is no problem when the nitrogen content is less than 50 ppm, but in this case, it is difficult to carry out purification. When the total nitrogen content in the polythiol compound is 50 to 600 ppm, significant deterioration of color phase of the polythiol compound is not caused for a long period of time, and even when using the polythiol compound after long-term preservation, the color phase of resin obtained is deteriorated just slightly, and it is not required to change the blending amount of a blueing agent or the like. Moreover, for example, it is not required to perform temperature control for preventing deterioration of the polythiol compound, and accordingly, not only the improvement of physical properties of lenses, but also cost reduction can be realized.

The total nitrogen content can be deceased to some extent by acid washing of the polythiol compound, but it is difficult to decrease the total nitrogen content to 600 ppm or less only by acid washing. For this reason, a production method which can decrease the total nitrogen content has been desired.

Hereinafter, the method for producing the polythiol compound of the present invention will be described in detail using the compound of formula (1) as an example.

A polyalcohol represented by formula (2) below, which is a raw material of the polythiol compound of formula (1), is synthesized by reacting epichlorohydrin with 2-mercaptoethanol in the presence of an alkali:

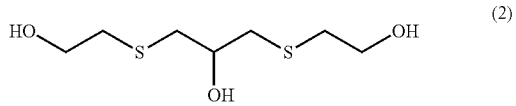 [SMILES: OCCSCC(O)CSCCO]

(2)

The synthesized polyalcohol is reacted with thiourea in a mineral acid, and a thiuronium salt obtained is subjected to hydrolysis with at least one base selected from the group consisting of hydrazine (hydrate), ammonia and an amine (hereinafter sometimes referred to as "amine-based base") and an inorganic base (that is different from hydrazine (hydrate) or ammonia) in the presence of an organic solvent, thereby obtaining the polythiol represented by formula (1). The hydrazine (hydrate) means hydrazine or hydrazine hydrate.

Specifically, in a method for synthesizing the polythiol compound represented by formula (1) from the polyalcohol represented by formula (2), for example, a thiuronium salt production step and a hydrolysis step are carried out as described below. In the thiuronium salt production step, to the polyalcohol represented by formula (2), thiourea in an amount of 3 equivalents or more (equivalent to the hydroxy group in the molecule) and less than 5 equivalents (2 equivalents excess), and preferably 1.1 equivalents relative to the hydroxy group, i.e., 3.3 equivalents or more and less than 4 equivalents (1 equivalent excess) relative to polyalcohol is added to be reacted. When the amount of thiourea is small, the purity of polythiol obtained is reduced, and when the amount is too large, the remaining amount of unreacted raw materials is increased and it is economically unfavorable. The reaction is performed at a temperature in the range of from room temperature to the reflux temperature in an aqueous solution of a mineral acid in an amount of 3 equivalents or more, and preferably 3 equivalents or more and 6 equivalents or less relative to the polyalcohol represented by formula (2). As the mineral acid, hydrochloric acid, hydrobromic acid, hydroiodic acid, sulfuric acid, phosphoric acid, etc. can be used. From the viewpoint of a sufficient reaction rate and control of coloring of products, hydrochloric acid is preferred.

Next, in the hydrolysis reaction, the above-described reaction solution is mixed with the organic solvent with stirring while a base comprising the amine-based base and the inorganic base is added thereto. The organic solvent is not particularly limited as long as the reaction is progressed thereby, but preferably used are ethers, aromatic hydrocarbons and halogenated hydrocarbons. Specific examples thereof include diethyl ether, benzene, toluene, xylene, dichloroethane, chloroform and chlorobenzene. Among them, toluene is preferred. By coexistence of the organic solvent during hydrolysis, the effect of removing the nitrogen component in the polythiol compound can be improved. By performing hydrolysis with an appropriate amount of the base being added, the produced polythiol can be rapidly extracted in the organic layer, and the effect of separating the nitrogen component from the polythiol compound can be obtained.

Examples of the at least one base selected from the group consisting of hydrazine (hydrate), ammonia and amine to be added in the hydrolysis step include ammonia, hydrazine (hydrate), methylamine, ethylamine, propylamine, isopropylamine, butylamine, dimethylamine, diethylamine, diisopropylamine, dipropylamine and dibutylamine. Among them, preferred is at least one compound selected from the group consisting of ammonia, hydrazine (hydrate), methylamine, ethylamine, propylamine, isopropylamine and butylamine, more preferred are ammonia and hydrazine (hydrate), and even more preferred is hydrazine (hydrate). As the hydrazine (hydrate), hydrazine hydrate is preferred. The amount of the at least one base selected from the group consisting of hydrazine (hydrate), ammonia and amine to be used in the hydrolysis step is 0.4 to 1.2 equivalents relative to the thiuronium group in the thiuronium salt compound, and more preferably 0.6 to 1 equivalent relative to the thiuronium group. When the amount of the at least one base selected from the group consisting of hydrazine (hydrate), ammonia and amine to be added is too small, the yield is reduced, and when the amount is too large, the total nitrogen content is increased.

Examples of the inorganic base to be used in the hydrolysis reaction include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Preferred are sodium hydroxide and potassium hydroxide, and more preferred is sodium hydroxide. The amount of the inorganic base to be added is set such that the total amount of the inorganic base and the amine-based base to be added becomes 0.9 to 3 equivalents, and more preferably 1 to 2 equivalents relative to the amount of mineral acid to be used in the step of the reaction of thiuronium salt production. When the amount is too small, the reaction proceeds insufficiently, and when the amount is too large, the yield is reduced.

The polythiol compound represented by formula (1) produced in this way can be purified by removing the organic layer and then carrying out acid washing, water washing, condensation and filtration.

The polyisocyanate compound to be used in the present invention is not particularly limited as long as it is a compound having at least two isocyanates in one molecule, and specific examples thereof include diethylene diisocyanate, tetramethylene diisocyanate, hexamethylene diisocyanate, trimethylhexamethylene diisocyanate, cyclohexane diisocyanate, 1,3-bis(isocyanatemethyl)cyclohexane, 1,4-bis(isocyanatemethyl)cyclohexane, isophorone diisocyanate, 2,6-bis(isocyanatemethyl)decahydronaphthalene, lysine triisocyanate, tolylene diisocyanate, o-tolidine diisocyanate, diphenylmethane diisocyanate, diphenylether diisocyanate, 3-(2'-isocyanatecyclohexyl)propylisocyanate, isopropylidene bis(cyclohexyl isocyanate), 2,2'-bis(4-isocyanatephenyl)propane, triphenylmethane triisocyanate, bis(diisocyanatetolyl)phenylmethane, 4,4',4''-triisocyanate-2,5-dimethoxyphenylamine, 3,3'-dimethoxybenzidine-4,4'-diisocyanate, 1,3-phenylene diisocyanate, 1,4-phenylene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(isocyanatemethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl diisocyanate, thiodipropyl diisocyanate, thiodihexyl diisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyl diisocyanate and dithiodipropyl diisocyanate.

Among them, at least one compound selected from the group consisting of isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane is a preferred specific example. Among them, more preferred are isophorone diisocyanate, tolylene diisocyanate, diphenylmethane diisocyanate, hexamethylene diisocyanate, 1,3-bis(isocyanatemethyl)cyclohexane and m-xylylene diisocyanate, even more preferred are isophorone diisocyanate, m-xylylene diisocyanate and 1,3-bis(isocyanatemethyl)cyclohexane, and most preferred is m-xylylene diisocyanate.

However, the polyisocyanate compound to be used in the present invention is not limited thereto, and these compounds may be used solely, or two or more of them may be used in combination.

The ratio (molar ratio) of the polyisocyanate compound to be used in the present invention is not particularly limited, but usually, NCO/(SH+OH) is 0.7 to 2.5, preferably 0.8 to 2.25, and more preferably 1.0 to 2.0. When the ratio is less than the above-described range, yellowing may be caused at the time of lens molding, and when the ratio is more than the above-described range, heat resistance may be reduced.

Examples of the episulfide compound to be used in the present invention include episulfides such as bis(β-epithiopropyl)sulfide, bis(β-epithiopropyl)disulfide, bis(β-epithiopropylthio)methane, 1,2-bis(β-epithiopropylthio)ethane, 1,3-bis(β-epithiopropylthio)propane and 1,4-bis(β-epithiopropylthio)butane. These compounds may be used solely, or two or more of them may be used in combination.

However, the episulfide compound to be used in the present invention is not limited thereto, and these compounds may be used solely, or two or more of them may be used in combination.

Among them, preferred are bis(β-epithiopropyl)sulfide and bis(β-epithiopropyl)disulfide, and most preferred is bis(β-epithiopropyl)sulfide.

In the present invention, a plurality of polythiol compounds may be used in combination. Polythiol compounds may be used solely, or two or more of them may be used in combination.

Specific examples thereof include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-timercaptopropane, 2-mercaptomethyl-1,3-dimercaptopropane, 2-mercaptomethyl-1,4-dimercaptobutane, 2-(2-mercaptoethylthio)-1,3-dimercaptopropane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercapto propionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol, 1,2-bis[(2-mercaptoethyl)thio]-3-mercaptopropane and 1,1,3,3-tetrakis(mercaptomethylthio)propane.

Among them, preferred are bis(2-mercaptoethyl)sulfide, 2,5-dimercaptomethyl-1,4-dithiane, 1,3-bis(mercaptomethyl)benzene, 1,4-bis(mercaptomethyl)benzene, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2-bis[(2-mercaptoethyl)thio]-3-mercaptopropane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate), more preferred are bis(2-mercaptoethyl) sulfide, 2,5-bis(2-mercaptomethyl)-1,4-dithiane, 1,3-bis(mercaptomethyl)benzene, pentaerythritol tetrakis-mercaptopropionate, 1,2-bis[(2-mercaptoethyl)thio]-3-mercaptopropane and pentaerythritol tetrakis-thioglycolate, and most preferred are 1,2-bis[(2-mercaptoethyl)thio]-3-mercaptopropane, bis(2-mercaptoethyl)sulfide and 2,5-dimercaptomethyl-1,4-dithiane.

When obtaining an optical material by polymerizing and curing the composition for optical materials of the present invention, it is preferred to add a polymerization catalyst thereto. As the polymerization catalyst, a publicly-known urethanation catalyst, episulfide polymerization catalyst or the like can be used. Preferably used are organotins, amines, phosphines and onium salts. Particularly preferably used are organotins and onium salts, and among them, organotins, quaternary ammonium salts and quaternary phosphonium salts are preferred.

The amount of the polymerization catalyst to be added cannot be determined categorically because it varies depending on the components of the composition, the mixing ratio and the method for polymerization and curing, but the amount is usually 0.0001% by mass to 10% by mass, preferably 0.001% by mass to 5% by mass, more preferably 0.01% by mass to 1% by mass, and most preferably 0.01% by mass to 0.5% by mass when the total amount of the composition for optical materials is 100% by mass. When the amount of the polymerization catalyst to be added is more than 10% by mass, the composition may be rapidly polymerized. When the amount of the polymerization catalyst to be added is less than 0.0001% by mass, the composition for optical materials may be insufficiently cured, resulting in poor heat resistance.

Moreover, in the production of the optical material of the present invention, it is surely possible to add additives such as an ultraviolet absorber, a blueing agent and a pigment to the composition for optical materials to further improve practicability of the optical material obtained.

Preferred examples of the ultraviolet absorber include benzotriazole-based compounds, and particularly preferred are 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol.

The amount of the ultraviolet absorber to be added is usually 0.01 to 5% by mass when the total amount of the composition for optical materials is 100% by mass.

When polymerizing and curing the composition for optical materials, publicly-known additives such as an internal mold release agent, an antioxidant and a polymerization modifier may be added according to need.

The composition for optical materials thus obtained is injected into a mold or the like and polymerized to obtain an optical material.

At the time of cast-molding the composition for optical materials of the present invention, it is preferred to filter and remove impurities using, for example, a filter having a pore diameter of about 0.1 to 5 μm in terms of improving the quality of the optical material of the present invention.

The composition for optical materials of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be suitably used as an optical lens.

EXAMPLES

Hereinafter, the present invention will be specifically described by way of a synthesis example, working examples and comparative examples. However, the present invention is not limited only to the working examples.

Preservation Stability Test of Polythiol Compound:
Polythiol was preserved under nitrogen atmosphere at 50° C. for 2 months.

ΔAPHA (Color Phase Change) of Polythiol Compound:
The APHA value of the polythiol compound before and after the preservation test at 50° C. for 2 months was measured using Hazen meter HM-4 (manufactured by X DENSHI SEKKEI, K.K.), and the amount of change (ΔAPHA) was obtained.

Total Nitrogen Content (TN) of Polythiol Compound:
The total nitrogen content of the produced polythiol compound was measured using TN-2100H (manufactured by Mitsubishi Chemical Analytech Co., Ltd.).

Color Phase Change (ΔYI Value) of Plastic Lens:
Resins (thickness: 10 mm, φ 83 mm) were prepared using polythiol compounds before and after the preservation test at 50° C. for 2 months. YI of each of the resins was measured using a spectroscopic colorimeter JS555 (manufactured by Color Techno System Corporation), and the difference between the values (ΔYI value) was obtained.

Synthesis Example (Synthesis of Polyalcohol Compound and Reaction of Thiuronium Salt Production)

76.0 parts by mass of water and 90.0 parts by mass (1.08 mol) of aqueous solution of sodium hydroxide (48% by mass) were put into a 2 L four-neck reaction flask equipped with a stirring machine, a reflux cooling tube, a nitrogen gas purge tube and a thermometer. 169 parts by mass (2.16 mol) of 2-mercaptoethanol was added dropwise thereto at 20° C. over 10 minutes, and after that, 99.9 parts by mass (1.08 mol) of epichlorohydrin was added dropwise thereto at the same temperature over 2 hours, then the temperature was increased to 30° C., and the mixture was matured for 1 hour.

Next, 450.1 parts by mass (4.44 mol) of water containing hydrochloric acid (36% by mass) and 271.7 parts by mass (3.57 mol) of thiourea were added thereto, and the mixture was heated to reflux at 110° C. for 3.5 hours to provide a thiuronium salt.

Example 1

The thiuronium salt synthesized in the synthesis example was cooled to 50° C., and 450.0 parts by mass of toluene was added thereto. After that, 97.5 parts by mass (1.95 mol) of hydrazine hydrate and 225.7 parts by mass (2.71 mol) of sodium hydroxide (48%) were added thereto with stirring so that the organic layer and the water layer were mixed homogeneously to perform a hydrolysis reaction for 2 hours, and after that, the water layer was allowed to be acidic, thereby obtaining a toluene solution of polythiol mainly composed of the compound represented by formula (1). The toluene solution was washed with 400 mL of 5% aqueous solution of sulfuric acid once and 400 mL of water twice, and after that, low-boiling components were removed under reduced pressure with heating and filtration was carried out, thereby obtaining 219 parts by mass of polythiol mainly composed of the compound of formula (1). The total nitrogen content of the obtained polythiol compound was 60 ppm, and the color phase change before and after the preservation stability test (ΔAPHA) was 0.

Examples 2 to 7

A polythiol comprising the compound of formula (1) as the main component was obtained in a manner similar to that in Example 1, except that the type and the equivalent ratio of each of the amine-based base and the inorganic base were changed. The results of analysis of such polythiols are shown in Table 1.

Comparative Examples 1 and 2

A polythiol comprising the compound of formula (1) as the main component was obtained in a manner similar to that in Example 1, except that the inorganic base was not added and only the amine-based base was used. The results of analysis of such polythiols are shown in Table 1.

Comparative Example 3

A polythiol comprising the compound of formula (1) as the main component was obtained in a manner similar to that in Example 1, except that the amine-based base was not added and only the aqueous solution of sodium hydroxide was used. The results of analysis of the polythiol are shown in Table 1.

Comparative Example 4

A polythiol comprising the compound of formula (1) as the main component was obtained in a manner similar to that in Example 1, except that a hydrolysis reaction was performed without the addition of toluene. The results of analysis of the polythiol are shown in Table 1.

Production of Thiourethane Resin 52 parts by mass of m-xylylene diisocyanate, 0.015 parts by mass of di-n-butyltin dichloride, 0.1 parts by mass of Zelec UN (manufactured by Stepan) and 0.05 parts by mass of Biosorb 583 (manufactured by Kyodo Chemical Co., Ltd.) were mixed together to be dissolved. 48 parts by mass of a polythiol mainly composed of the compound of formula (1) synthesized in each of the working examples and comparative examples and a polythiol after the preservation stability test were added thereto to be mixed at 15° C., thereby producing a mixed homogeneous solution. This mixed homogeneous solution was subjected to deforming at 600 Pa for 30 minutes. After that, it was filtered using a 1-μm PTFE filter and then injected into a mold made of a glass mold and a tape. This mold was put into an oven, and the temperature was gradually increased from 10° C. to 120° C. to perform polymerization for 20 hours. After the polymerization was completed, the mold was taken out from the oven, and a resin was obtained by being released from the mold. The obtained resin was further subjected to annealing at 130° C. for 2 hours, thereby obtaining an optical material made of thiourethane resin. The evaluation results of ΔYI of thiourethane resin using respective polythiols are shown in Table 1.

Production of Episulfide Resin

To 77 parts by mass of bis(β-epithiopropyl)sulfide, 9 parts by mass of 1,3-bis(isocyanatemethyl)benzene, and 14 parts by mass of a polythiol mainly composed of the compound of formula (1) synthesized in each of the working examples and comparative examples and a polythiol after the preservation stability test, 0.2 parts by mass of tetrabutylphosphonium bromide as a polymerization catalyst and 0.05 parts by mass of dibutyltin dichloride were added to obtain a homogeneous solution at room temperature. This mixed homogeneous solution was subjected to deforming at 600 Pa for 1 hour. After that, it was filtered using a 1-μm PTFE filter and then injected into a mold made of a glass mold and a tape. This mold was put into an oven, and it was heated from 20° C. to 100° C. over 20 hours to perform polymerization and curing. After that, demolding was carried out, thereby obtaining an optical material made of episulfide resin. The evaluation results of ΔYI of episulfide resin using respective polythiols are shown in Table 1.

TABLE 1

| | | Amine-based base | | | Inorganic base | | | Polythiol compound | | | |
|---|---|---|---|---|---|---|---|---|---|---|---|
| | Organic solvent | Type | Equivalents relative to polyalcohol compound | Equivalents relative to thiuronium group | Type | Equivalents relative to polyalcohol compound | Equivalents relative to thiuronium group | Total nitrogen content | ΔAPHA | Thiourethane resin ΔYI | Episulfide resin ΔYI |
| Example 1 | toluene | hydrazine | 1.8 | 0.6 | NaOH | 2.5 | 0.83 | 60 | 0 | 0 | 0 |
| Example 2 | toluene | hydrazine | 2.4 | 0.8 | NaOH | 2.4 | 0.80 | 103 | 1 | 0.2 | 0.1 |
| Example 3 | toluene | hydrazine | 3 | 1.0 | NaOH | 1.4 | 0.47 | 237 | 2 | 0.3 | 0.1 |
| Example 4 | toluene | ammonia | 3 | 1.0 | NaOH | 1.4 | 0.47 | 232 | 2 | 0.4 | 0.1 |
| Example 5 | toluene | hydrazine | 2.4 | 0.8 | KOH | 2.4 | 0.80 | 110 | 1 | 0.2 | 0.1 |
| Example 6 | toluene | hydrazine | 1.2 | 0.4 | NaOH | 3.0 | 1.0 | 340 | 4 | 0.4 | 0.2 |
| Example 7 | toluene | hydrazine | 3.6 | 1.2 | NaOH | 0.5 | 0.17 | 430 | 5 | 0.5 | 0.2 |
| Comparative Example 1 | toluene | hydrazine | 4.8 | 1.6 | — | 0 | 0 | 1350 | 16 | 2.1 | 0.9 |
| Comparative Example 2 | toluene | ammonia | 4.8 | 1.6 | — | 0 | 0 | 947 | 12 | 1.6 | 0.6 |
| Comparative Example 3 | toluene | — | 0 | 0.0 | NaOH | 4.8 | 1.6 | 990 | 11 | 1.5 | 0.6 |

TABLE 1-continued

| | Organic solvent | Amine-based base | | | Inorganic base | | Polythiol compound | | Thiourethane resin ΔYI | Episulfide resin ΔYI |
|---|---|---|---|---|---|---|---|---|---|---|
| | | Type | Equivalents relative to polyalcohol compound | Equivalents relative to thiuronium group | Type | Equivalents relative to polyalcohol compound | Equivalents relative to thiuronium group | Total nitrogen content | ΔAPHA | | |
| Comparative Example 4 | not used | hydrazine | 1.8 | 0.6 | NaOH | 2.5 | 0.83 | 1310 | 14 | 1.7 | 0.7 |

According to the results in Table 1, it is understood that ΔAPHA (color phase change) of the polythiol compound of the present invention is low (0 to 5) and it is excellent. Meanwhile, ΔAPHA (color phase change) of the polythiol compound of each of Comparative Examples 1 to 4 is 11 to 16, and it is inferior to the present invention. Further, it is understood that the ΔYI value (color phase change) of thiourethane resin using the polythiol compound of the present invention is low (0 to 0.5) and it is excellent. Meanwhile, the ΔYI value (color phase change) of thiourethane resin using the polythiol compound of each of Comparative Examples 1 to 4 is 1.5 to 2.1, and it is inferior to the present invention. Moreover, it is understood that the ΔYI value (color phase change) of episulfide resin using the polythiol compound of the present invention is low (0 to 0.2) and it is excellent. Meanwhile, the ΔYI value (color phase change) of episulfide resin using the polythiol compound of each of Comparative Examples 1 to 4 is 0.6 to 0.9, and it is inferior to the present invention.

The invention claimed is:

1. A composition comprising a polythiol compound and a nitrogen component, wherein the composition has a total nitrogen content of 50 to 600 ppm.

2. The composition comprising a polythiol compound according to claim 1, wherein the polythiol compound has a structure represented by formula (1) below:

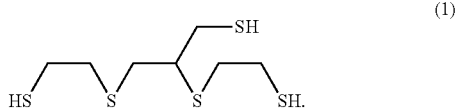

(1)

3. A composition for optical materials comprising the composition according to claim 1 and further comprising a polyisocyanate compound.

4. An optical material obtained by polymerizing and curing the composition for optical materials according to claim 3.

5. A composition for optical materials comprising the composition according to claim 1 and further comprising an episulfide compound.

6. A method for producing the composition according to claim 1, which comprises:
   i) reacting a polyalcohol with thiourea to prepare a thiuronium salt; and
   ii) adding to the thiuronium salt in the presence of an organic solvent
      a) an inorganic base other than hydrazine, hydrazine hydrate, and ammonia and
      b) at least one base selected from the group consisting of:
         i) hydrazine,
         ii) hydrazine hydrate,
         iii) ammonia, and
         iv) an amine,
   to hydrolyze the thiuronium salt.

7. The method for producing the composition according to claim 6, wherein the organic solvent is at least one selected from the group consisting of diethyl ether, benzene, toluene, xylene, dichloroethane, chloroform and chlorobenzene.

8. The method for producing the composition according to claim 6, wherein the inorganic base is at least one selected from the group consisting of sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide.

9. The method for producing the composition according to claim 6, wherein the amount of the at least one base selected from the group consisting of hydrazine (hydrate), ammonia and amine to be added is 0.4 to 1.2 equivalents relative to the thiuronium group in the thiuronium salt.

* * * * *